United States Patent
Carbonelli et al.

(10) Patent No.: US 11,428,658 B2
(45) Date of Patent: Aug. 30, 2022

(54) GAS SENSING DEVICE AND METHOD FOR OPERATING A GAS SENSING DEVICE

(71) Applicant: Infineon Technologies AG, Neubiberg (DE)

(72) Inventors: Cecilia Carbonelli, Munich (DE); Manuel Carro Dominguez, Dublin (IE); Jianyu Zhao, Munich (DE)

(73) Assignee: INFINEON TECHNOLOGIES AG, Neubiberg (DE)

( * ) Notice: Subject to any disclaimer, the term of this patent is extended or adjusted under 35 U.S.C. 154(b) by 392 days.

(21) Appl. No.: 16/777,065

(22) Filed: Jan. 30, 2020

(65) Prior Publication Data

US 2020/0271605 A1 Aug. 27, 2020

(30) Foreign Application Priority Data

Feb. 25, 2019 (EP) .................................... 19159173

(51) Int. Cl.
*G01N 27/12* (2006.01)
*G06N 3/04* (2006.01)
(Continued)

(52) U.S. Cl.
CPC ............ *G01N 27/123* (2013.01); *G06N 3/04* (2013.01); *G06N 3/08* (2013.01); *G01N 27/122* (2013.01); *G01N 33/0034* (2013.01)

(58) Field of Classification Search
USPC ......................................................... 702/24
See application file for complete search history.

(56) References Cited

U.S. PATENT DOCUMENTS

| 10,508,988 B2* | 12/2019 | Sagberg | G01N 33/0062 |
| 2009/0144022 A1* | 6/2009 | Li | G16H 50/50 |
| | | | 702/179 |
| 2013/0064423 A1* | 3/2013 | Joseph | G06V 10/30 |
| | | | 382/103 |

FOREIGN PATENT DOCUMENTS

| CN | 101806763 | 8/2010 |
| WO | 2018201201 | 11/2018 |

OTHER PUBLICATIONS

Boiger, Romano et al., "Exploring Temperature-Modulated Operation Mode of Metal Oxide Gas Sensors for Robust Signal Processing", Proceedings of Eurosensors 2018, Graz, Sep. 2018, 5 pages.

(Continued)

*Primary Examiner* — Paul D Lee
(74) *Attorney, Agent, or Firm* — Slater Matsil, LLP

(57) ABSTRACT

A gas sensing device includes one or more chemo-resistive gas sensors; one or more heating elements for heating each of the gas sensors; a preprocessing block for filtering signal samples in order to generate filtered signal samples for each of the gas sensors; an information extraction block for generating representations for the filtered signal samples for each of the gas sensors based on dynamic characteristics of the received filtered signal samples of the respective gas sensor; and a decision making block for receiving the representations, wherein the decision making block includes a trained model based algorithm stage having an input layer and an output layer, wherein the decision making block includes trained models, wherein the decision making block creates sensing results based on output values of the output layer of the algorithm stage, and wherein the output values are created by using the trained models.

20 Claims, 12 Drawing Sheets

(51) Int. Cl.
*G06N 3/08* (2006.01)
*G01N 33/00* (2006.01)

(56) References Cited

OTHER PUBLICATIONS

Cho, Jung Hwan et al., "Wireless electronic nose system for real-time quantitative analysis of gas mixtures using micro-gas sensor array and neuro-fuzzy network", Sensors and Actuators, B, 134, Apr. 23, 2008, pp. 104-111.

Corcoran, P., et al., "Optimal configuration of a thermally cycled gas sensor array with neural network pattern recognition", Elsevier, Sensors and Actuators, B, 48, May 30, 1998, pp. 448-455.

Jaeschke, Carsten et al., "A Novel Modular eNose System Based on Commercial MOX Sensors to Detect Low Concentrations of VOCs for Breath Gas Analysis", mdpi.com/journal/proceeedings, Proceedings of Eurosensors 2018, Graz, Sep. 2018, 4 pages.

Gutierrez-Osuna, Ricardo "Pattern Analysis for Machine Olfaction: A Review," IEEE Sensors Journal, vol. 2, No. 3, Jun. 2002, pp. 189-202.

Lipatov, Alexey et al., "Highly selective gas sensor arrays based on thermally reduced graphene oxide", Nanoscale, The Royal Society of Chemistry, Apr. 2013, 5, 5426-5434.

Vergara, Alexander et a., "Optimized Feature Extraction for Temperature-Modulated Gas Sensor", Hindawi Publishing Corporation, Journal of Sensors, vol. 2009, Article ID 716316, Apr. 2009, 11 pages.

Yin, Xin et al., "Temperature Modulated Gas Sensing E-Nose System for Low-Cost and Fast Detection", IEEE Sensors Journal, vol. 16, No. 2, Jan. 15, 2016, pp. 464-474.

\* cited by examiner

GAS SENSING DEVICE AND METHOD FOR OPERATING A GAS SENSING DEVICE

This application claims the benefit of European Patent Application No. 19159173, filed on Feb. 25, 2019, which application is hereby incorporated herein by reference.

TECHNICAL FIELD

Embodiments relate to a gas sensing device for sensing one or more gases in a mixture of gases. Further embodiments relate to a method for operating such gas sensing device. More particularly, the disclosure deals with the estimation of gas concentrations through the use of chemo-resistive gas sensors.

BACKGROUND

Chemical sensor algorithms are either limited to a simple model for the proof of sensor functionality, or based on a geographically distributed sensor systems.

Other existing publications describe complicated pattern analysis models based on large amount of data obtained from geographically distributed sensor systems.

SUMMARY

A gas sensing device for sensing one or more gases in a mixture of gases is provided; the gas sensing device comprises:

one or more chemo-resistive gas sensors, wherein each of the gas sensors is configured for generating signal samples corresponding to a concentration of one of the one or more gases in the mixture of gases, wherein the one or more gas sensors are alternately operated in recovery phases and in sense phases, wherein the signal samples SIG of each of the gas sensors are generated during the sense phases;

one or more heating elements for heating each of the gas sensors, wherein the one or more heating elements are brought to a first temperature during the recovery phases and to a second temperature during the sense phases, wherein the first temperature is higher than the second temperature;

a preprocessing block configured for receiving the signal samples from each of the gas sensors and for filtering the received signal samples in order to generate filtered signal samples for each of the gas sensors;

an information extraction block configured for receiving the filtered signal samples and for generating representations for the received filtered signal samples for each of the gas sensors based on dynamic characteristics of the received filtered signal samples of the respective gas sensor; and a decision making block configured for receiving the representations, wherein the decision making block comprises a trained model based algorithm stage having an input layer and an output layer, wherein the decision making block comprises one or more trained models for the algorithm stage, wherein the representations for each of the gas sensors are input to the input layer of the algorithm stage, wherein the decision making block creates for each of the gas sensors sensing results based on output values of the output layer of the algorithm stage, wherein the output values for each of the gas sensors are created by using at least one of the one or more trained models at the algorithm stage so that the output values for each of the gas sensors depend on the representations of each of the gas sensors.

The one or more chemo-resistive gas sensors may be reduced graphene oxide gas sensors, where the base material is functionalized with specific chemicals, e.g. with palladium (Pd), platinum (Pt), or manganese dioxide (MnO2), so that each of the gas sensors is sensitive for a specific gas, e.g. for nitrogen dioxide (NO2), ozone (O3) or carbon monoxide (CO). In doing so, the interaction between graphene sheets and absorbed gas analytes influences the electronic structure of the material depending on the mixture of gases, resulting in altered charge carrier concentration and changed electrical conductance.

In case of multi-gas sensing a multi-gas sensor array comprising a plurality of chemo-resistive gas sensors having dissimilar selectivity may be used. Due to the different sensitivity towards various gas molecules, resistances of the gas sensors change in disparate patterns, making it possible to analyze complicated gas mixtures with one single sensor array.

Each of the gas sensors may be heated by one or more heating elements. The temperature of the one or more heating elements is pulsed between a first temperature during the recovery phases of the gas sensors and a second temperature during the sense phases of the gas sensors, wherein the first temperature is higher than the second temperature. The first temperature may be, for example, set to 300° C., whereas the second temperature may be, for example, set to 200° C. The result of these controlled temperature oscillations is a more dynamic behavior of the responses of the gas sensors which will be exploited by the gas sensing device as described below. In order to improve repeatability and stability of the sensing results, only the portion of the responses of the gas sensors at the lower temperatures, i.e. after switching from the first temperature to the second temperature, may be considered.

The preprocessing block is configured for suppressing and/or compensating of artifacts in the signal samples and/or noise in the signal samples and/or invalid signal samples due to malfunctioning gas sensors and/or errors in the signal samples due to drifts of the gas sensors in order to produce more reliable filtered signal samples.

The information extraction block is configured for transforming the filtered signal samples into representations, wherein the representations are based on dynamic characteristics of the filtered signal samples. To this end, the pulsed nature of the responses of the gas sensors is leveraged and characteristics are extracted which rely on the dynamic evolution of the gas sensors.

The decision making block comprises a trained model based algorithm stage. A trained model based algorithm stage is a processing stage which is capable of machine learning. The machine learning is done in a preoperational training phase in which trained models are developed by comparing actual output values of the trained model based algorithm stage with desired output values of the trained model based algorithm stage for defined inputs of the trained model based algorithm stage. The trained models have a predefined structure, wherein a parametrization of the predefined structure is done during the training phase. The trained models comprise the learned content after the training phase is finished. In an operational phase for producing sensing results one or more of the trained models from the training phase are used to process the representations from the information extraction block.

In the training phase the plurality of trained models can be established and afterwards stored at the decision-making block. The trained models may differ in the structures and/or the parameters. During operation of phase the most appropriate trained model may be selected depending on the on the specific use-case.

The decision making block provides a decision on the classification of gas concentrations detected by the gas sensors or a continuous measurement of gas concentrations detected by the gas sensors. In the first case a trained model, which is trained as a classification algorithm, is used and the sensing results are alphanumeric terms such as "high" or "low". In the latter case a trained model, which is trained as a regression algorithm, is used in the sensing results our physical quantities such as "4% by volume".

The gas sensing device according to the disclosure addresses the intrinsic instability of chemo-resistive gas sensors. It uses robust algorithms and detection mechanisms which can cope with calibration inaccuracies, drifts and other similar effects reliably and over a wide operating range.

The proposed gas sensing device provides an end to end solution for multi-gas adsorption sensors which is versatile, widely-applicable to multiple applications and uses cases (outdoor, indoor, health check, etc.) and can be embedded in a smart portable device. Specifically, an algorithm is used that works on continuous sensor readings, makes use of the transient information in the sensor responses and exhibits low complexity and limited memory requirements.

The gas sensing device can reflect real world scenarios, where, for example, gas mixtures are present which are causing cross-sensitivities in the sensor responses. Moreover, the gas sensing device only takes a short time for reaching a stable response level.

The material costs of the gas sensing device are low and it uses concrete mechanisms which are robust and economic enough to be embedded into mass-produced consumer electronic products (like a mobile phone), while delivering good continuous prediction performance in complicated real world scenarios, and as such have to deal with challenges related to the availability of a limited and noisy sets of data, imperfect initial calibration, gas mixtures with varying concentrations of analytes, modelling errors, etc.

In particular, the gas sensing device may be used for air quality monitoring.

According to embodiments of the disclosure the gas sensing device comprises one or more auxiliary sensors, wherein each of the auxiliary sensors is configured for generating auxiliary signal samples corresponding to a physical quantity of operating conditions of the gas sensing device;

wherein the one or more auxiliary sensors comprise:

a first temperature sensor for generating first auxiliary signal samples of the auxiliary signal samples, which correspond to a temperature of the one or more heating elements, and/or a second temperature sensor for generating second auxiliary signal samples of the auxiliary signal samples, which correspond to an ambient temperature of the gas sensing device, and/or a humidity sensor for generating third auxiliary signal samples of the auxiliary signal samples, which correspond to an ambient humidity of the gas sensing device.

By these features the accuracy of the gas sensing device may be further increased.

According to embodiments of the disclosure the decision making block is configured for selecting one or more selected trained models from the one or more trained models based on the auxiliary signal samples of the one or more auxiliary sensors, wherein the output values for the one or more gas sensors are created by using the one or more selected trained models.

For example the most appropriate trained model could be chosen based on the humidity value obtained from a humidity sensor as humidity has an impact on the dynamics of the sensor responses and thus on the mode.

By these features the accuracy of the gas sensing device may be further increased.

According to embodiments of the disclosure the preprocessing block is configured for receiving the auxiliary signal samples from each of the auxiliary sensors and for filtering the received auxiliary signal samples in order to generate filtered auxiliary signal samples for each of the auxiliary sensors;

wherein the information extraction block is configured for receiving the filtered auxiliary signal samples and for generating auxiliary representations for the received filtered auxiliary signal samples for each of the auxiliary sensors based on dynamic characteristics of the received filtered auxiliary signal samples of the respective auxiliary sensor; and wherein the decision making block is configured for inputting the auxiliary representations for each of the auxiliary sensors to the input layer of the algorithm stage so that the output values for the one or more gas sensors depend on the auxiliary representations of each of the auxiliary sensors.

By these features the accuracy of the gas sensing device may be further increased.

According to embodiments of the disclosure the algorithm stage comprises a neural network using the one or more trained models and/or a random decision forest using the one or more trained models.

An artificial neural network is a parameterized statistic model, in which a number of logistic regressions are combined nonlinearly. Such systems "learn" to perform tasks by considering examples, generally without being programmed with any task-specific rules. A neural network is based on a collection of connected nodes called artificial neurons. Each connection can transmit a signal from one artificial neuron to another. An artificial neuron that receives a signal can process it and then signal additional artificial neurons connected to it. The structure of the nodes, or the hyperparameters, of a neural network is predefined by a model and the parameters of the connections are found by training the neural network. Structure and the corresponding parameters form a trained model for the respective neural network.

A random decision forest is a learning method for classification, regression and other tasks that operates by constructing a multitude of decision trees at training time and outputting the class that is the mode of the classes (classification) or mean prediction (regression) of the individual trees.

According to embodiments of the disclosure the one or more trained models comprise one or more trained multiple-output models having a plurality of outputs, wherein for all of the gas sensors the output values for the respective gas sensor are created by using one of the trained multiple-output models at the algorithm stage, wherein each of the output values is created at a different output of the plurality of outputs.

According to embodiments of the disclosure for each of the gas sensors the one or more trained models comprise one or more trained single-output models having a single output, wherein the output values for the different of the gas sensors are created by using different single-output models of the trained single-output models at the algorithm stage.

According to embodiments of the disclosure the preprocessing block comprises a baseline manipulation stage configured for transforming the signal samples of each of the gas sensors into a relative resistance change according to a baseline of the signal samples of the respective gas sensor.

Baseline manipulation is the transformation of a signal sample of one of the gas sensors into a relative resistance change with respect to sensor response to a reference analyte, wherein such sensor response is called a baseline. Synthetic air is a very common baseline as it is easily applicable and realistic in a real world scenario. The purpose of a baseline is to potentially create a more stable and reproducible sensing result by removing some of the drift caused by long term gas exposure and ageing of the sensor. As shown in Equation (1), subtracting the sensor response by its baseline Ro removes additive drift while division removes multiplicative drift. Using both operations combined results in the relative resistance change $\Delta R/Ro$:

$$\Delta R/Ro = (R-Ro)/Ro \qquad (1).$$

According to embodiments of the disclosure the preprocessing block comprises a defect detection stage configured for a detection of defects of the gas sensing device, wherein the detection is based on the auxiliary signal samples of one or of the more auxiliary sensors. The defect detection stage may be configured for detecting defects at the one or more heating elements on a basis of the first auxiliary signal samples of the first temperature sensor. If such a defect is detected, signal samples which are established while the defect occurs, may be discarded from further processing.

According to embodiments of the disclosure the preprocessing block comprises an artefact detection stage configured for a detection of artefacts in the signal samples of each of the gas sensors, wherein the detection for each of the gas sensors is based on comparing of sequential signal samples of the respective gas sensor.

As the complexity of experiments increases, certain environmental conditions, such as changes in temperature, humidity and presence of other gases, can produce discontinuities in the sensor's response if there are desynchronizations between lab apparatuses. These discontinuities appear as sudden spikes in the signal samples which with adequate detection, by checking if the difference in value of two sequential signal samples surpasses a threshold, can be easily removed. This difference doesn't necessarily have to be calculated from the signal sample but rather from the apparatus causing the anomaly in the signal sample.

According to embodiments of the disclosure the preprocessing block comprises a moving mean filter stage configured for reducing noise in the filtered signal samples for each of the gas sensors.

Noise in the signal samples can originate from accuracy limitations of apparatus. For example, the current resistance measurement can only round to the nearest ohm. It is important to remove noise as it can cause pattern recognition algorithms to detect patterns that are exclusive to the noise produced in a particular situation. As shown in noise can be reduced using a central as it converts the resistance value at time t to the average resistance value between $t-\tau$ and $t+\tau$. The moving mean filter stage may be a cascaded integrator-comb filter stage.

According to embodiments of the disclosure the information extraction block comprises one or more feature extraction stages, wherein each of the feature extraction stages is configured for calculating a feature of one of the filtered signal samples for each of the gas sensors, wherein each of the features refers to the dynamic characteristics of the received filtered signal samples of the respective gas sensor.

In order to extract relevant information out of the signal samples and transform them into features which provide meaningful data to the decision making block, a combination of feature extraction stage as may be used.

According to embodiments of the disclosure the feature extraction stages comprise a derivative calculation stage configured for calculating a derivative of the one of the filtered signal samples for each of the gas sensors, wherein the derivative is one of the features of the one of the filtered signal samples.

The gas sensors are operated in adsorption phases that increase or decrease the sensor resistance depending on the gas to which the gas sensor is exposed to. This is an important sensor characteristic as it differentiates between an adsorption and desorption phase even if a sensor has the same response value in both phases. In other words, using the derivative of a filtered signal sample as a feature (Equation 2), pattern recognition algorithms are able to differentiate between adsorption and desorption phases.

$$D_{n,i} = \frac{R_{n,i+1} - R_{n,i-1}}{t_{n,i+1} - t_{n,i-1}} \qquad (2)$$

for $1<i<N$, $n=1, 2, \ldots 8$, where n is the sensor number, R and D are the preprocessed sensor responses and their derivatives respectively.

It has to be noted that the absorption/desorption phase information obtained using (2) can guide in the selection of the trained model in the decision making block.

According to embodiments of the disclosure the feature extraction stages comprise a phase space integral calculation stage configured for calculating a phase space integral of the one of the filtered signal samples for each of the gas sensors, wherein the phase space integral is one of the features of the one of the filtered signal samples.

A phase space is a model used within dynamic systems to capture the change in a system state over time. In this phase space the temporal evolution of any system is represented by time parametric trajectories. The signal and its first time derivative are the two canonical variables commonly used to produce the phase space. For our results we used the integral of this trajectory which condenses the magnitude of the interaction with its velocity. This can be seen as the combination of the two already mentioned features, sensor response and the corresponding derivative. Containing dynamic and steady-state information, new characteristics of the sensor signals are created that a pattern recognition algorithm may not have been identified by analyzing magnitude and velocity separately. Since the integral of this trajectory distinguishes between signals with similar dynamic behavior and the same resistance shift, it can be a contributing feature to estimate both gas concentration (quantitative analysis) and class membership (qualitative analysis).

According to embodiments of the disclosure the feature extraction stages comprise a correlation calculation stage configured for calculating of a time correlation for each of the gas sensors between the one of the filtered signal samples and a previous filtered signal sample of the signal samples of the respective gas sensor, wherein the time correlation is one of the features of the one of the filtered signal samples, and/or a spatial correlation between the one of the filtered signal samples and one of the filtered signal samples of another of the gas sensors, wherein the spatial correlation is one of the features of the one of the filtered signal samples.

Given the dynamic behavior of the gas sensors, the availability of several transient in the sensor responses and the characteristic array structure with different functionalizations, it makes sense to introduce metrics which exploits such time and spatial properties. This can be achieved introducing a time autocorrelation function of the normalized sensor responses of the type (and its derivative)

$$R_\tau = \Sigma_{k=1}^{n} x_k y_k \quad (3)$$

Where x and y indicate the normalized response at different moments in time (or, alternatively, their derivatives) and n is the window size being used to calculate the autocorrelation. Particularly:

$$x_k = \frac{\Delta R(k)}{R_0}; x_k = \Delta R(k+\tau)/R_0 \quad (4)$$

Similarly, the correlation among the different gas sensors should also be exploited with a spatial correlation matrix of the type:

$$R_s[r, p] = \frac{1}{n}\sum_{i=1}^{n} x_{i,r} x_{i,p} \quad (5)$$

According to embodiments of the disclosure the feature extraction stages comprise a dynamic moment calculation stage configured for calculating of a dynamic moment of the one of the filtered signal samples for each of the gas sensors, wherein the dynamic moment is one of the features of the one of the filtered signal samples.

The phase space integral neglects the characteristics proper of the signal evolution. For example, dynamic properties resulting from different interactions taking place by sensors being exposed to different analytes are neglected by the features like derivative or integral of phase space. To this end, the shape of the trajectory in the space described by the signal response plotted against the same signal response delayed by T samples is introduced. It should be noted that the interactions with different compounds (sensor functionalization) result in different trajectories and therefore greater consistent differentiation among samples that can help pattern recognition algorithms classify multi-gas exposures.

The differences in trajectories are recorded by the following set of morphological descriptors, also known as dynamic moments. Analogous to the second moments of area of a 2-D geometrical feature, these are used to obtain the dynamic moments.

$$DM3_{PB} = \frac{\sqrt{2}}{2n}\sum_{i=1}^{n}(x_i^2 y_i - x_i y_i^2) \quad (6)$$

$$DM3_{SB} = \frac{\sqrt{2}}{2n}\sum_{i=1}^{n}[2x_i^3 + 3(x_i^2 y_i + x_i y_i^2)] \quad (7)$$

$$DM3_X = \frac{1}{2n}\sum_{i=1}^{n}(x_i^3 + 3x_i y_i^2) \quad (8)$$

$$DM3_Y = \frac{1}{2n}\sum_{i=1}^{n}(x_i^3 + 3x_i^2 y_i) \quad (9)$$

The number gives the degree of the moment, the subscript indicates the direction along which the moment is calculated, PB and SB are principle and secondary bi-sectors, is the window size being used to calculate the dynamic moments, i.e. the number of prior samples that are used to calculate the dynamic moments at the current moment in time. x and y indicate the normalized response at different moments in time as in (4).

According to embodiments of the disclosure the information extraction block is configured in such way that one of the representations comprises all of the features of the one of the filtered signal samples.

According to embodiments of the disclosure the information extraction block comprises a dimensionality reduction stage, wherein each of a plurality of the features of the one of the filtered signal samples is fed to dimensionality reduction stage, wherein the dimensionality reduction stage is configured to output one or more reduced features based on the plurality of the features fed to the dimensionality reduction stage, wherein a number of the reduced features is smaller than a number of the features fed to the dimensionality reduction stage, wherein a redundancy of the reduced features is lower than a redundancy of the features fed to the dimensionality reduction stage, wherein the information extraction block is configured in such way that one of the representations comprises all of the reduced features of the one of the filtered signal samples.

The feature space (the dimensionality of the features) may be reduced, for example to 2 or 3 dimensions. If the non-linear behavior in the reduced representation needs to be captured, an auto-encoder may be used for dimensionality reduction. An auto-encoder is an unsupervised learning algorithm that works similarly to a feed-forward neural network but instead of trying to classify an input, it is trying to reproduce the input as the output by minimizing the reconstruction error. This is particularly useful because the hidden layer of the auto-encoder has fewer neurons than the input layer.

The representation in the hidden layer (feature layer) of a 3-layer auto encoder will produce similar results to principal component analysis except the scale of the reduced dimensions will be different. More hidden layers can help encode more complex functions of the input which can help find non-linear interdependencies among features.

Furthermore, to escape "curse of dimensionality", avoid redundancy and further reduce noise, the dimension of the extracted features may be reduced through an auto-encoder. Compared to more traditional dimensionality reduction methods such as principal component analysis and linear discriminant analysis, the use of an auto-encoder has the additional benefit of capturing also nonlinearities in the original signal representation which otherwise would be lost and cannot be exploited to discriminate the different gases.

According to embodiments of the disclosure the decision making block comprises a low pass filter for filtering the output values of the output layer of the algorithm stage for each of the gas sensors, wherein the sensing results are output values of the low pass filter.

In a classification problem, after obtaining a predicted label from the test set using the trained model, a post-processing is also applied to the output, where a percentile filter may be used to remove erroneous anomalies. In a regression problem, a filter which synchronizes with the sensor temperature and smooths the oscillations caused by temperature pulsing may be combined with a percentile filter which removes outliers. It should be noted that a percentile filter with 50% percentile coincides with a median filter.

Further disclosed is a method for operating a gas sensing device for sensing one or more gases in a mixture of gases, the gas sensing device comprising one or more chemoresistive gas sensors:

using each of the gas sensors for generating signal samples corresponding to a concentration of one of the one or more gases in the mixture of gases, wherein the one or more gas sensors are alternately operated in recovery phases and in sense phases, wherein the signal samples of each of the sensors are generated during the sense phases;

heating each of the gas sensors by using one or more heating elements, wherein the one or more heating elements are brought to a first temperature during the recovery phases and to a second temperature during the sense phases, wherein the first temperature is higher than the second temperature;

using a preprocessing block for receiving the signal samples from each of the gas sensors and for filtering the received signal samples in order to generate filtered signal samples for each of the gas sensors;

using an information extraction block for receiving the filtered signal samples and for generating representations for the received filtered signal samples for each of the gas sensors based on dynamic characteristics of the received filtered signal samples of the respective gas sensor; and using a decision making block, which comprises an trained model based algorithm stage and one or more trained models for the algorithm stage, wherein the algorithm stage an input layer and an output layer, for receiving the representations, wherein the representations for each of the gas sensors are input to the input layer of the algorithm stage, for creating for each of the gas sensors sensing results based on output values of the output layer of the algorithm stage, wherein the output values for the one or more gas sensors are created by using at least one of the one or more trained models at the algorithm stage so that the output values for each gas sensor of the one or more gas sensors depend on the representations of each of the gas sensors.

BRIEF DESCRIPTION OF THE DRAWINGS

Embodiments of the present invention are described herein making reference to the appended drawings.

Figure 1:
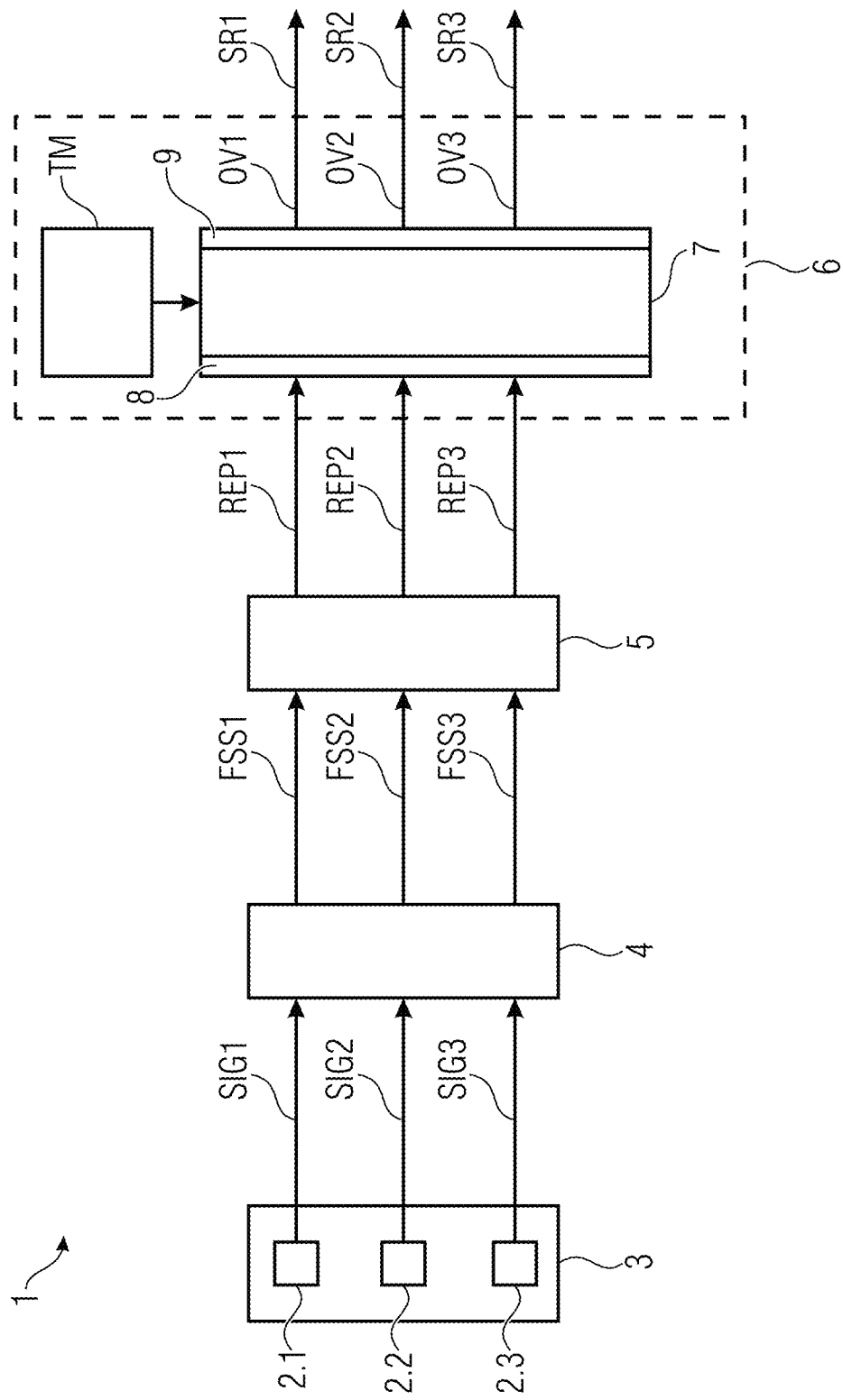
FIG. 1 shows a schematic view of a first embodiment of a gas sensing device comprising three chemo-resistive gas sensors.

Equal or equivalent elements or elements with equal or equivalent functionality are denoted in the following description by equal or equivalent reference numerals.

DETAILED DESCRIPTION OF ILLUSTRATIVE EMBODIMENTS

In the following description, a plurality of details is set forth to provide a more thorough explanation of embodiments of the present invention. However, it will be apparent to those skilled in the art that embodiments of the present invention may be practiced without these specific details. In other instances, well known structures and devices are shown in block diagram form rather than in detail in order to avoid obscuring embodiments of the present invention. In addition, features of the different embodiments described hereinafter may be combined with each other, unless specifically noted otherwise.

FIG. 1 shows a schematic view of a first embodiment of a gas sensing device 1 for sensing one or more gases in a mixture of gases. According to embodiments of the disclosure the gas sensing device 1 comprises:

one or more chemoresistive gas sensors 2, wherein each of the gas sensors 2 is configured for generating signal samples SIG corresponding to a concentration of one of the one or more gases in the mixture of gases, wherein the one or more gas sensors 2 are alternately operated in recovery phases and in sense phases, wherein the signal samples SIG of each of the gas sensors 2 are generated during the sense phases;

one or more heating elements 3 for heating each of the gas sensors 2, wherein the one or more heating elements 3 are brought to a first temperature during the recovery phases and to a second temperature during the sense phases, wherein the first temperature is higher than the second temperature;

a preprocessing block 4 configured for receiving the signal samples SIG from each of the gas sensors 2 and for filtering the received signal samples SIG in order to generate filtered signal samples FSS for each of the gas sensors 2;

an information extraction block 5 configured for receiving the filtered signal samples FSS and for generating representations REP for the received filtered signal samples FSS for each of the gas sensors 2 based on dynamic characteristics of the received filtered signal samples FSS of the respective gas sensor 2; and a decision making block 6 configured for receiving the representations REP, wherein the decision making block 6 comprises a trained model based algorithm stage 7 having an input layer 8 and an output layer 9, wherein the decision making block 6 comprises one or more trained models TM for the algorithm stage 7, wherein the representations REP for each of the gas sensors 2 are input to the input layer 8 of the algorithm stage 7, wherein the decision making block creates 6 for each of the gas sensors 2 sensing results SR based on output values OV of the output layer 9 of the algorithm stage 7, wherein the output values OV for each of the gas sensors 2 are created by using at least one of the one or more trained models TM at the algorithm stage 7 so that the output values OV for each of the gas sensors 2 depend on the representations REP of each of the gas sensors 2.

The embodiment shown in FIG. 1 comprises three chemoresistive gas sensors 2.1, 2.2 and 2.3, wherein each of the sensors 2.1, 2.2 and 2.3 is sensitive for a specific gas. For example, the gas sensor 2.1 may be nitrogen dioxide sensor, the gas sensor 2.2 may be an ozone sensor and the gas sensor 2.3 may be a carbon monoxide sensor. In some embodiments gas sensors 2 could be used, which are all sensitive to one or more gases, like nitrogen dioxide, but which react differently. In other embodiments, the number of gas sensors could be greater or smaller than three.

The gas sensor 2.1 produces signal samples SIG1 which are filtered by the preprocessing block 4 so that filtered signal samples FSS1 are obtained. The filtered signal samples FSS1 are transformed by the information extraction block 5 into representations REP1. The gas sensor 2.2 produces signal samples SIG2 which are filtered by the preprocessing block 4 so that filtered signal samples FSS2 are obtained. The filtered signal samples FSS2 are transformed by the information extraction block 5 into representations REP2. The gas sensor 2.3 produces signal samples SIG3 which are filtered by the preprocessing block 4 so that filtered signal samples FSS3 are obtained. The filtered signal samples FSS3 are transformed by the information extraction block 5 into representations REP3.

The representations REP1, REP2 and REP3 are fed to the input layer 8 of the algorithm stage 7 of the decision-making block 6. The representations REM1, REP2 and REP3 are simultaneously used for generating the output values OV1, OV2 and OV3 at the output layer 9 of the algorithm stage 7 by using one of the trained models TM.

In a further aspect the disclosure refers to a method for operating a gas sensing device 1 for sensing one or more gases in a mixture of gases, the gas sensing device 1 comprising one or more chemo-resistive gas sensors 2, wherein the method comprises the steps of:

using each of the gas sensors 2 for generating signal samples SIG corresponding to a concentration of one of the one or more gases in the mixture of gases, wherein the one or more gas sensors 2 are alternately operated in recovery phases and in sense phases, wherein the signal samples SIG of each of the sensors 2 are generated during the sense phases;

heating each of the gas sensors 2 by using one or more heating elements 3, wherein the one or more heating elements 3 are brought to a first temperature during the recovery phases and to a second temperature during the sense phases, wherein the first temperature is higher than the second temperature;

using a preprocessing block 4 for receiving the signal samples SIG from each of the gas sensors 2 and for filtering the received signal samples SIG in order to generate filtered signal samples FSS for each of the gas sensors 2;

using an information extraction block 5 for receiving the filtered signal samples FFS and for generating representations REP for the received filtered signal samples FFS for each of the gas sensors 2 based on dynamic characteristics of the received filtered signal samples FFS of the respective gas sensor 2; and using a decision making block 6, which comprises a trained model based algorithm stage 7 and one or more trained models TM for the algorithm stage 7, wherein the algorithm stage 7 has an input layer 8 and an output layer 9, for receiving the representations REP, wherein the representations REP for each of the gas sensors 2 are input to the input layer 8 of the algorithm stage 7, for creating for each of the gas sensors 2 sensing results SR based on output values OV of the output layer 9 of the algorithm stage 7, wherein the output values OV for the one or more gas sensors 2 are created by using at least one of the one or more trained models TM at the algorithm stage 7 so that the output values OV for each gas sensor 2 of the one or more gas sensors 2 depend on the representations REP of each of the gas sensors 2.

The disclosure provides a method for real time air quality monitoring embedded in a smart sensor. The proposed method comprises the following steps:
- preprocessing the responses of the gas sensors, e.g. for reducing noise and for eliminating artifacts,
- extracting the relevant information exploiting the dynamic nature of the temperature pulsed sensor responses,
- providing a representation of the sensed signal to the decision making block,
- decision making by using a trained model based algorithm.

The most appropriate trained model for the decision making block may be selected out of a given pool of trained models depending on the specific system application or use in order to make a prediction on the gas concentration or on the air quality level. Predictions may then be post-processed with a percentile filter in order to further improve the performance.

Moreover, the proposed solution may
- perform continuous and real-time measurements of the sensor responses
- extract statistic and transient information from all measurement samples, rather than performing a qualitative analysis of stable state samples only,
- predict various gas concentrations out of a single array of co-located sensors on a highly compact embedded system, instead of relying on a large number of cheap MOX sensors in a geographically distributed system, and
- provide an adaptive solution to different working conditions.

Figure 2:
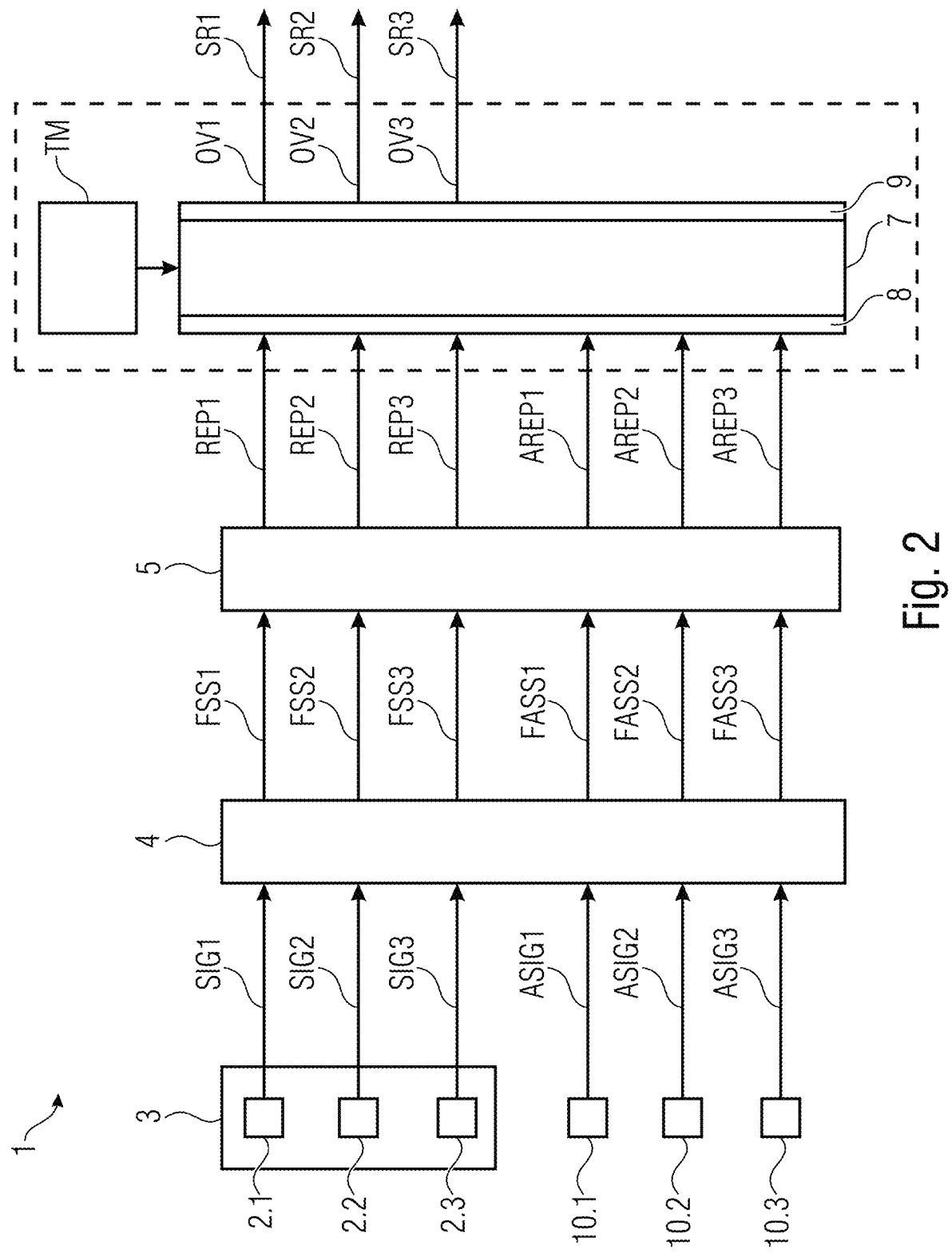
FIG. 2 shows a schematic view of a second embodiment of a gas sensing device comprising three chemo-resistive gas sensors and three auxiliary sensors.

FIG. 2 shows a schematic view of a second embodiment of a gas sensing device 1 for sensing one or more gases in a mixture of gases. The second embodiment is based on the first embodiment. According to embodiments of the disclosure the gas sensing device 1 additionally comprises:

one or more auxiliary sensors 10, wherein each of the auxiliary sensors 10 is configured for generating auxiliary signal samples ASIG corresponding to a physical quantity of operating conditions of the gas sensing device 1;

wherein the one or more auxiliary sensors 10 comprise a first temperature sensor 10.1 for generating first auxiliary signal samples ASIG1 of the auxiliary signal samples ASIG, which correspond to a temperature of the one or more heating elements 3, and/or a second temperature sensor 10.2 for generating second auxiliary signal samples ASIG2 of the auxiliary signal samples ASIG, which correspond to an ambient temperature of the gas sensing device 1, and/or a humidity sensor 10.3 for generating third auxiliary signal samples ASIG3 of the auxiliary signal samples ASIG, which correspond to an ambient humidity of the gas sensing device 1.

According to embodiments of the disclosure the decision making block 6 is configured for selecting one or more selected trained models TM from the one or more trained models TM based on the auxiliary signal samples ASIG of the one or more auxiliary sensors 10, wherein the output values OV for the one or more gas sensors 2 are created by using the one or more selected trained models TM.

According to embodiments of the disclosure the preprocessing block 4 is configured for receiving the auxiliary signal samples ASIG from each of the auxiliary sensors 10 and for filtering the received auxiliary signal samples ASIG in order to generate filtered auxiliary signal samples FASS for each of the auxiliary sensors 10;

wherein the information extraction block 5 is configured for receiving the filtered auxiliary signal samples FASS and for generating auxiliary representations AREP for the received filtered auxiliary signal samples AFSS for each of the auxiliary sensors 10 based on dynamic characteristics of the received filtered auxiliary signal samples FASS of the respective auxiliary sensor 10; and wherein the decision making block 6 is configured for inputting the auxiliary representations AREP for each of the auxiliary sensors 10 to the input layer 8 of the algorithm stage 7 so that the output values OV for the one or more gas sensors 2 depend on the auxiliary representations AREP of each of the auxiliary sensors 10.

The embodiment shown in FIG. 2 comprises three auxiliary sensors 10.1, 10.2 and 10.3, wherein each of the auxiliary sensors 10.1, 10.2 and 10.3 is sensitive for a specific physical quantity of operating conditions of the gas sensing device 1. For example, the auxiliary sensor 10.1 may be a first temperature sensor 10.1 for generating first auxiliary signal samples ASIG1 of the auxiliary signal samples ASIG, which correspond to a temperature of the one or more heating elements 3, the auxiliary sensor 10.2 may be a second temperature sensor 10.2 for generating second auxiliary signal samples ASIG2 of the auxiliary signal samples ASIG, which correspond to an ambient temperature of the gas sensing device 1 and the auxiliary sensor 2.3 may be a humidity sensor 10.3 for generating third auxiliary signal samples ASIG3 of the auxiliary signal samples ASIG, which correspond to an ambient humidity of the gas sensing device 1.

The auxiliary sensor 10.1 produces auxiliary signal samples ASIG1 which are filtered by the preprocessing block 4 so that filtered auxiliary signal samples FASS1 are obtained. The filtered auxiliary signal samples FASS1 are transformed by the information extraction block 5 into auxiliary representations AREP1. The auxiliary sensor 10.2 produces auxiliary signal samples ASIG2 which are filtered by the preprocessing block 4 so that filtered auxiliary signal samples FASS2 are obtained. The filtered auxiliary signal samples FASS2 are transformed by the information extraction block 5 into auxiliary representations AREP2. The auxiliary sensor 10.3 produces auxiliary signal samples ASIG3 which are filtered by the preprocessing block 4 so that filtered auxiliary signal samples FASS3 are obtained. The filtered auxiliary signal samples AFSS3 are transformed by the information extraction block 5 into auxiliary representations AREP3.

The representations REP1, REP2 and REP3 and the auxiliary representations AREP1, AREP2 and AREP3 are fed to the input layer 8 of the algorithm stage 7 of the decision-making block 6. The representations REP1, REP2 and REP3 and the auxiliary representations AREP1, AREP2 and AREP3 are simultaneously used for generating the output values OV1, OV2 and OV3 at the output layer 9 of the algorithm stage 7 by using one of the trained models TM.

Figure 3:
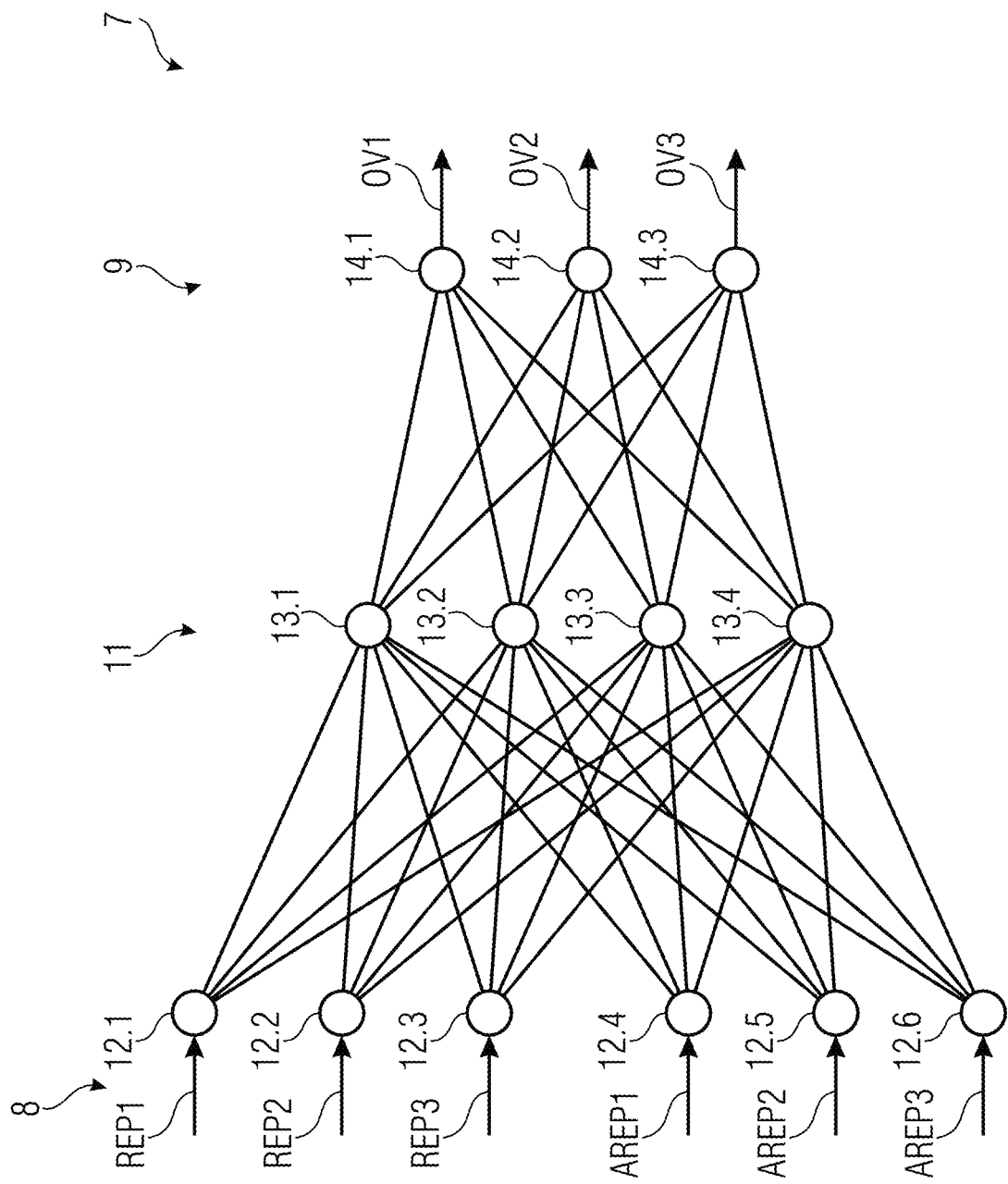
FIG. 3 schematically illustrates an algorithm stage comprising a neural network using a trained multiple-output model.

FIG. 3 schematically illustrates an algorithm stage comprising a neural network 11 using a trained multiple-output model TM.

According to embodiments of the disclosure the algorithm stage 7 comprises a neural network 11 using the one or more trained models TM and/or a random decision forest using the one or more trained models TM.

According to embodiments of the disclosure the one or more trained models TM comprise one or more trained multiple-output models TM having a plurality of outputs 14, wherein for all of the gas sensors 2 the output values OV for the respective gas sensor 2 are created by using one of the trained multiple-output models TM at the algorithm stage 7, wherein each of the output values OV is created at a different output 14 of the plurality of outputs 14.

In the embodiment of FIG. 3 the input layer 8 of the neural network 11 comprises six inputs 12.1 to 12.6. Each of the representations REP1, REP2 and REP3 and the auxiliary representations AREP1, AREP2 and AREP3 are fed to one of the inputs 12.1 to 12.6. Each of the inputs 12.1 to 12.6 is connected to each of the hidden nodes 13.1 to 13.4. Each of the hidden nodes 13.1 to 13.4 is connected to each of the outputs 14.1 to 14.3. The output 14.1 provides the output value OV1, the output 14.2 provides the output value OV2 and an output 14.3 provides the output value OV3. The described structure is given by the selected trained module TM which is a trained multiple-output model TM as it comprises a plurality of outputs 14.1 to 14.3. Parameters for the connections between the inputs 12.1 to 12.6 and the hidden nodes 13.1 to 13.4 as well as for collections between the hidden nodes 13.1 to 13.4 2 the outputs 14.1 to 14.3 have been determined during a preoperational training phase.

Figure 4:
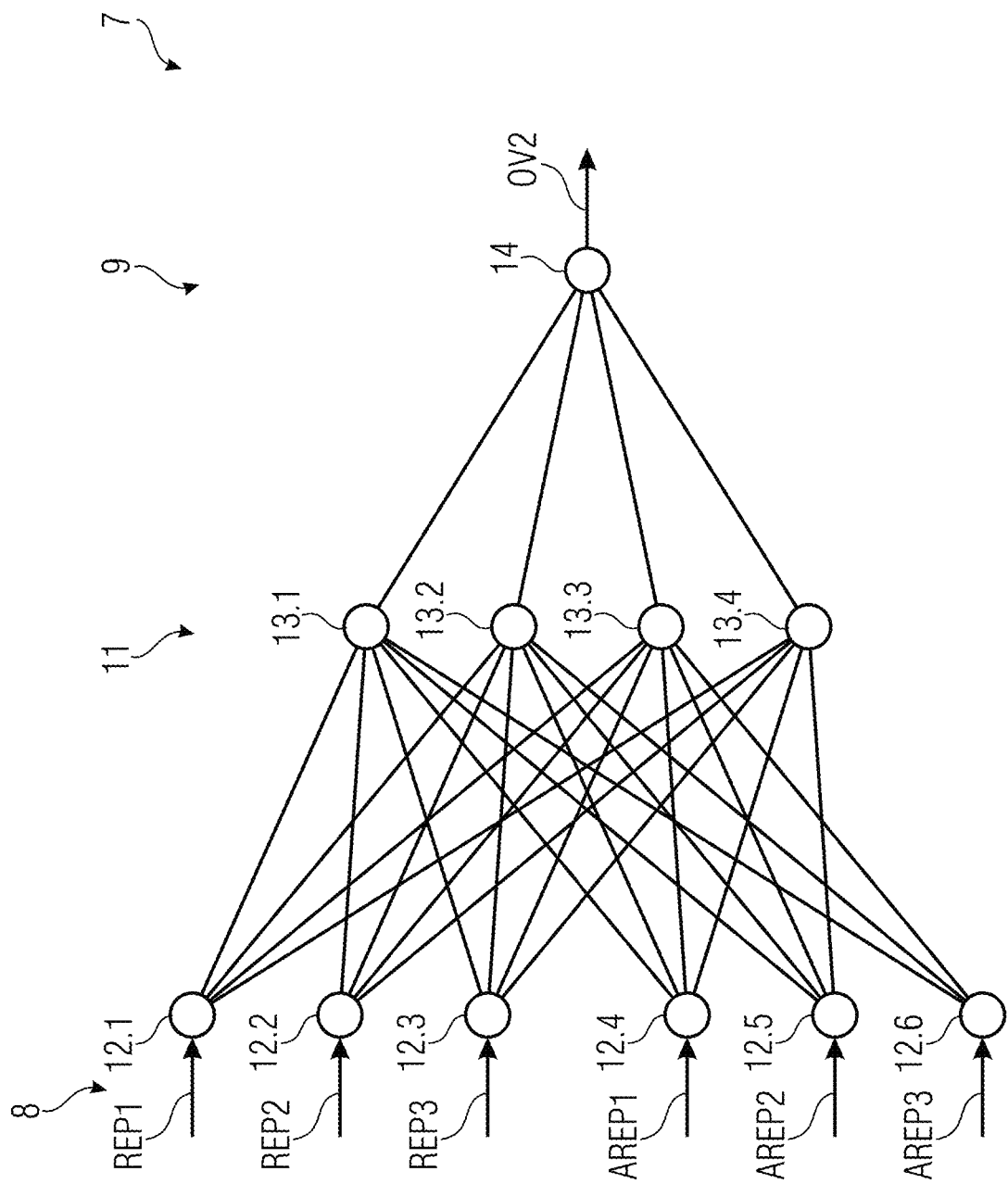
FIG. 4 schematically illustrates an algorithm stage comprising a neural network using a trained single-output model.

FIG. 4 schematically illustrates an algorithm stage comprising a neural network using a trained single-output model.

According to embodiments of the disclosure the one or more trained models TM comprise, for each of the gas sensors 2, one or more trained single-output models TM having a single output 14, wherein the output values OV for different gas sensors 2 of the gas sensors 2 are created by using different single-output models TM of the trained single-output models TM at the algorithm stage 7.

In the embodiment of FIG. 4 the input layer 8 of the neural network 11 comprises six inputs 12.1 to 12.6. Each of the representations REP1, REP2 and REP3 and the auxiliary representations AREP1, AREP2 and AREP3 are fed to one of the inputs 12.1 to 12.6. Each of the inputs 12.1 to 12.6 is connected to each of the hidden nodes 13.1 to 13.4. Each of the hidden nodes 13.1 to 13.4 is connected to the outputs 14. The output 14 provides the output value OV1 while using a first trained model TM, the output value OV2 while using second trained model TM and the output value OV3 wire using a third friend model TM. The described structure is given by the selected trained module TM which is a trained single model TM as it comprises only one output 14. Parameters for each of the trained models for the connections between the inputs 12.1 to 12.6 and the hidden nodes 13.1 to 13.4 as well as for collections between the hidden nodes 13.1 to 13.4 2 the outputs 14.1 to 14.3 have been determined during a preoperational training phase.

For the neural network 11, a small number of input nodes 12, e.g. 6 or 8 input nodes 12, one or two layers of hidden nodes 13 and a logistic activation function were sufficient to obtain good results.

Also, for regression one may observe slightly better results with three single-output models TM, each one trained on a different class, compared to one single large model TM with multiple-output trained on three gases at the same time.

Figure 5:
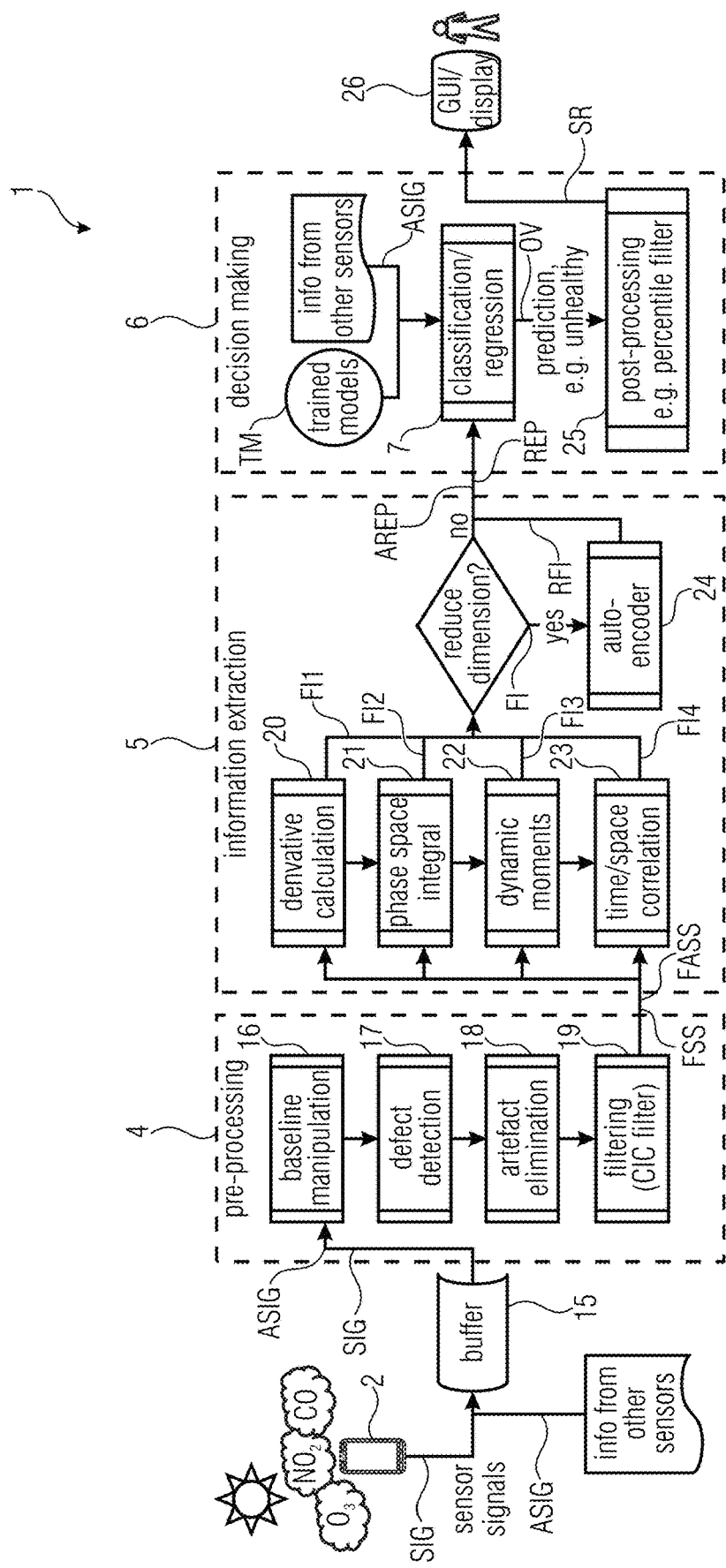
FIG. 5 shows a schematic view of a third embodiment of a gas sensing device.

FIG. 5 shows a schematic view of a third embodiment of a gas sensing device.

According to embodiments of the disclosure the preprocessing block 4 comprises a baseline manipulation stage 16 configured for transforming the signal samples SIG of each of the gas sensors 2 into a relative resistance change according to a baseline of the signal samples SIG of the respective gas sensor 2.

According to embodiments of the disclosure the preprocessing block 4 comprises a defect detection stage 17 configured for a detection of defects of the gas sensing device 1, wherein the detection is based on the auxiliary signal samples ASIG of one or of the more auxiliary sensors 10.

According to embodiments of the disclosure the preprocessing block 4 comprises an artefact detection stage 18 configured for a detection artefacts in the signal samples SIG of each of the gas sensors 2, wherein the detection for each of the gas sensors 2 is based on comparing of sequential signal samples SIG of the respective gas sensor 2.

According to embodiments of the disclosure the preprocessing block 4 comprises a moving mean filter stage 19 configured for reducing noise in the filtered signal samples FSS for each of the gas sensors 2.

According to embodiments of the disclosure the information extraction block 5 comprises one or more feature extraction stages 20, 21, 22, 23, wherein each of the feature extraction stages 20, 21, 22, 23 is configured for calculating a feature FI of one of the filtered signal samples FSS for each of the gas sensors 2, wherein each of the features refers to the dynamic characteristics of the received filtered signal samples FSS of the respective gas sensor 2.

According to embodiments of the disclosure the feature extraction stages 20, 21, 22, 23 comprise a derivative calculation stage 20 configured for calculating a derivative of the one of the filtered signal samples FSS for each of the gas sensors 2, wherein the derivative is one of the features FI of the one of the filtered signal samples FFS.

According to embodiments of the disclosure the feature extraction stages 20, 21, 22, 23 comprise a phase space integral calculation stage 21 configured for calculating a phase space integral of the one of the filtered signal samples FFS for each of the gas sensors 2, wherein the phase space integral is one of the features FI of the one of the filtered signal samples FFS.

According to embodiments of the disclosure the feature extraction stages 20, 21, 22, 23 comprise a correlation calculation stage 23 configured for calculating of a time correlation for each of the gas sensors 2 between the one of the filtered signal samples FFS and a previous filtered signal sample FFS of the signal samples FFS of the respective gas sensor 2, wherein the time correlation is one of the features FI of the one of the filtered signal samples FFS.

According to embodiments of the disclosure the feature extraction stages 20, 21, 22, 23 comprise a correlation calculation stage 23 configured for calculating of a spatial correlation between the one of the filtered signal samples FFS and one of the filtered signal samples FFS of another of the gas sensors 2, wherein the spatial correlation is one of the features FI of the one of the filtered signal samples FFS.

According to embodiments of the disclosure the feature extraction stages 20, 21, 22, 23 comprise a dynamic moment calculation stage 22 configured for calculating of a dynamic moment of the one of the filtered signal samples FFS for each of the gas sensors 2, wherein the dynamic moment is one of the features FI of the one of the filtered signal samples FFS.

According to embodiments of the disclosure the information extraction block 5 is configured in such way that one of the representations REP comprises all of the features FI of the one of the filtered signal samples FFS.

According to embodiments of the disclosure the information extraction block 5 comprises a dimensionality reduction stage 24, wherein each of a plurality of the features FI of the one of the filtered signal samples FFS is fed to dimensionality reduction stage 24, wherein the dimensionality reduction stage 24 is configured to output one or more reduced features RFI based on the plurality of the features FI fed to the dimensionality reduction stage 24, wherein a number of the reduced features RFI is smaller than a number of the features FI fed to the dimensionality reduction stage 24, wherein a redundancy of the reduced features RFI is lower than a redundancy of the features FI fed to the dimensionality reduction stage 24, wherein the information extraction block 5 is configured in such way that one of the representations REP comprises all of the reduced features RF of the one of the filtered signal samples FFS.

According to embodiments of the disclosure the decision making block 6 comprises a low pass filter 25 for filtering the output values OV of the output layer 9 of the algorithm stage 7 for each of the gas sensors 2, wherein the sensing results SR are output values of the low pass filter 25.

In the embodiment of FIG. 5 signal samples SIG of one or more gas sensor 2 and auxiliary signal samples ASIG are fed to a buffer 15. The buffer 15 may be a circular first in first out buffer (FIFO-buffer) configured to store the past N signal samples, where N represents the window size used in the upcoming filtering process. A new sample with signals from one of the gas sensors or one of the auxiliary other is added to the queue, while the oldest sample in the queue is deleted. The middle sample of the queue (with order N/2) is then sent to the preprocessing block 4.

The preprocessing block 4 comprises in this order a baseline manipulation stage 16, a defect detection stage 17, an artifact detection stage 18 and a moving mean filter stage 19, which are connected in series. However order of these stages could be different.

The signal sample SIG of one of the gas sensors to is first transformed into relative resistance change according to its baseline, i.e. sensor response to a reference analyte such as synthetic air in the lab, so that the signal sample SIG can be more stable and reproducible. With information provided by the auxiliary sensors 10, such as heater temperatures and environment temperature, it is possible to detect defective sensors and to eliminate the corresponding sample accordingly. Artifacts introduced in measurement, such as sharp spikes, can also be detected and eliminated. Last but not least, the signals are filtered with a CIC filter, given neighboring samples from the buffer 15 and the last intermediate result. The new intermediate result will replace the old one, while filtered signal samples FSS and filtered auxiliary samples FASS are then sent to the information extraction block 5.

The information extraction block 5 comprises a derivate calculation stage 20, a phase space integral calculation stage 21, a dynamic moment calculation stage 22 and a correlation calculation stage 23, which are arranged in parallel. The derivate calculation stage 20 outputs the feature F1, the phase space integral calculation stage 21 outputs the feature F2, the dynamic moment calculation stage 22 outputs the feature F3 and the correlation calculation stage 23 outputs the feature F4 for each of the filtered signal samples FSS and for each of the filtered auxiliary signal samples FASS.

The features F1 to F4 may be directly sent to the decision-making block 6 in order to serve as the representation REP for one of the filtered signal samples FSS or as the auxiliary representation AREP for one of the filtered auxiliary signal samples FASS.

The features F1 to F4 may also be sent to the dimensionality reduction stage 24 which produces one or more reduced features RFI, which may be sent to the decision-making block 6 in order to serve as the representation REP for one of the filtered signal samples FSS or for one of the filtered auxiliary signal samples FASS.

The output values OV of the algorithm stage 7 are filtered by a low pass filter 25 which outputs the sensing results SR. The sensing results SR may be fed to a user interface 26.

With the extracted features and other information, trained models are used to predict the air quality level of the environment, which is called decision making. Note that information from auxiliary sensors 10, such as ambient temperature and humidity, can either work as additional features FI (and included in the training) or be used to select the most appropriate trained model TM from multiple trained ones. Prediction obtained from the trained models TM is then post-processed, for example, filtered to eliminate outliers or smooth oscillations, and sent to a user interface 26 so that the user can read it directly.

In order to predict the gas concentration several supervised algorithms can be applied. However, for embedded applications where the memory requirements for the operational part of the algorithm are quite stringent, one may be focused on feed forward neural networks for classification and/or regression since this solution has shown the best performance in combination with 'dynamic' types of features FI (such as correlation, phase space integral or dynamic moments). The choice between classification and regression depends on whether a discrete output is desired such as one of the air quality index categories in Table 1 or whether a ppb/ppm resolution is needed for the gas. In other words, it depends on the customer requirements on the device 1.

TABLE 1

| | Gas concentration (8 h average) | | | |
| --- | --- | --- | --- | --- |
| Gas | Good | Moderate | Very poor | Unhealthy |
| $NO_2$ | 0-50 ppb | 50-100 ppb | 100-600 ppb | >600 ppb |
| Ozone | 0-50 ppb | 50-100 ppb | 100-400 ppb | >400 ppb |
| CO | 0-2 ppm | 2-10 ppm | 10-30 ppm | >30 ppm |

Figure 6:
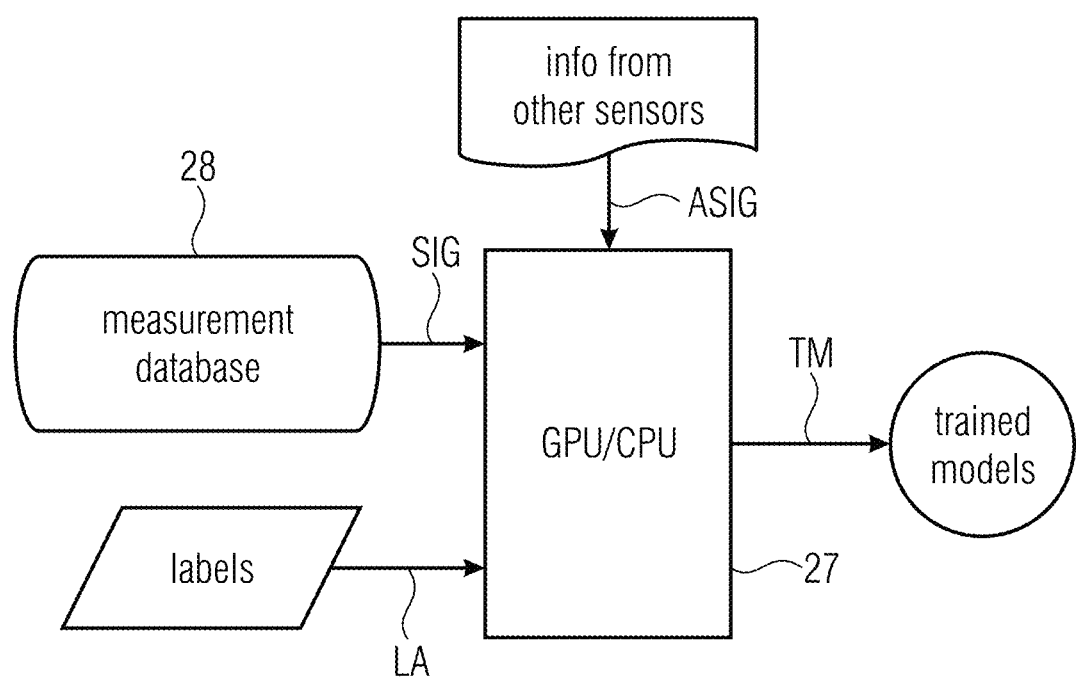
FIG. 6 illustrates an exemplary training phase in order to produce trained models for the algorithm stage.

FIG. 6 illustrates an exemplary training phase in order to produce trained models TM for the algorithm stage 7. The model training can be performed on a processing unit 27, such as a graphics processing unit (GPU) or a central processing unit (CPU). In the training phase illustrated in FIG. 6, signal samples SIG from a measurement database 28, optionally labels LA for the purpose of classification, and auxiliary signal samples ASIG from auxiliary sensors 10 (e.g., corresponding to ambient temperature and humidity) are given to the processing unit 27 in order to optimize parameters of one of the trained models TM.

Figure 7:
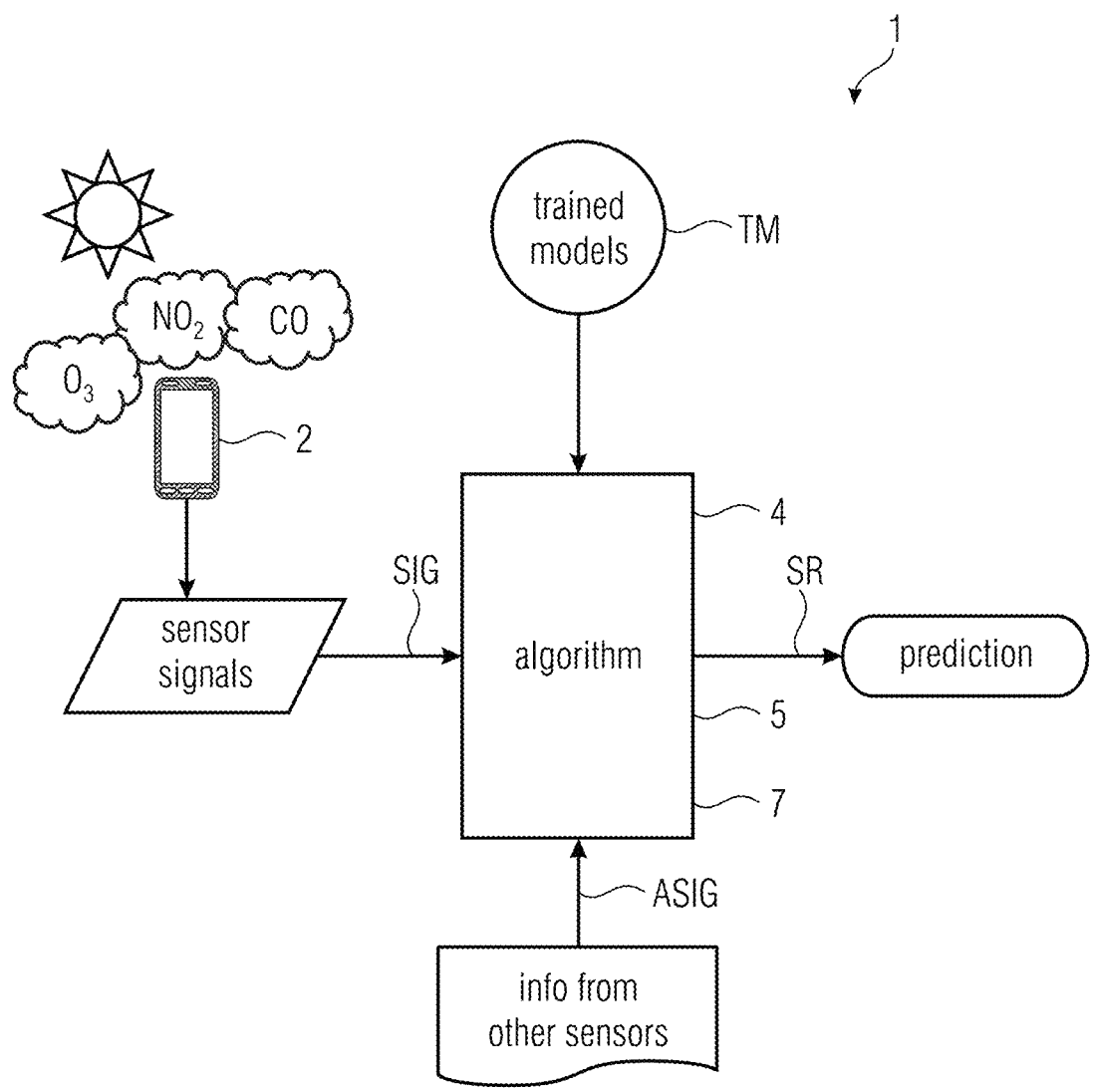
FIG. 7 illustrates an exemplary operating phase of the gas sensing device.

FIG. 7 illustrates an exemplary operating phase of the gas sensing device 1. The gas sensing device 1 may be an embedded device having less computational power the processing unit 27.

The trained models TM established by the processing unit 27 during the training phase are used by the gas sensing device during the operational phase in order to predict air quality based on signal samples SIG from one or more gas sensors 2 and from auxiliary signal samples ASIG of one or more auxiliary sensors 10 in real time. With the gas sensors 2, optionally the auxiliary sensors 10 and the stages 4, 5, 6 embedded in a portable device 1, for example in a smartphone, the user can read air quality level with the lowest latency on the go. It has to be noted that multiple trained models TM can be made available and then depending on the desired output for the specific application (outdoor monitoring, indoor monitoring, etc.) the most appropriate one will be selected during the operational phase.

Figure 8:
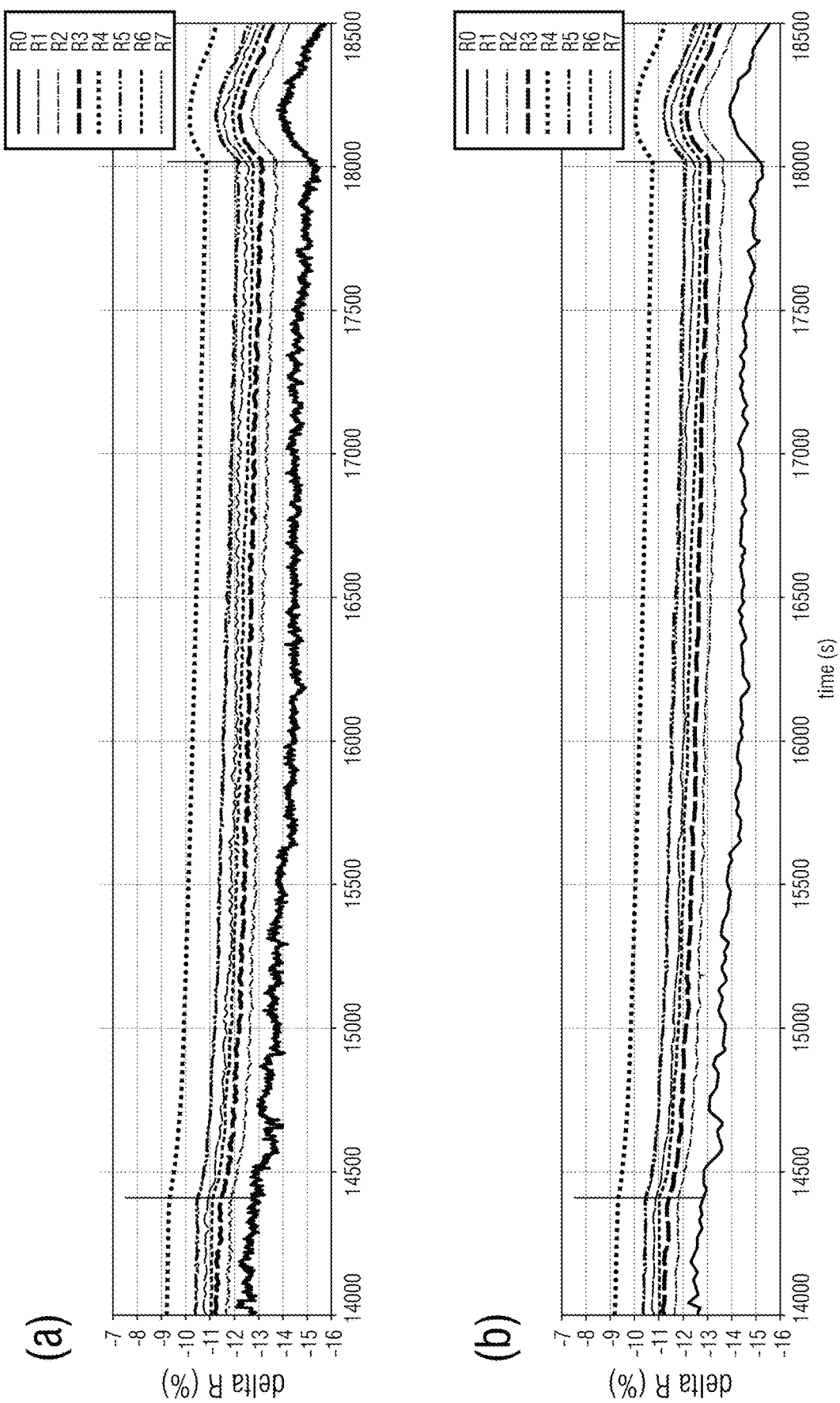
FIG. 8 illustrates exemplary filtered signal samples.

FIG. 8 illustrates exemplary filtered signal samples FFS. In portion (a) exemplary filtered signal samples FFS, which are produced by using a baseline manipulation stage 16 only, are shown. In portion (b) exemplary filtered signal samples FFS, which are produced by using an artefact detection stage 18 and a moving mean filter stage 19, are shown.

Figure 9:
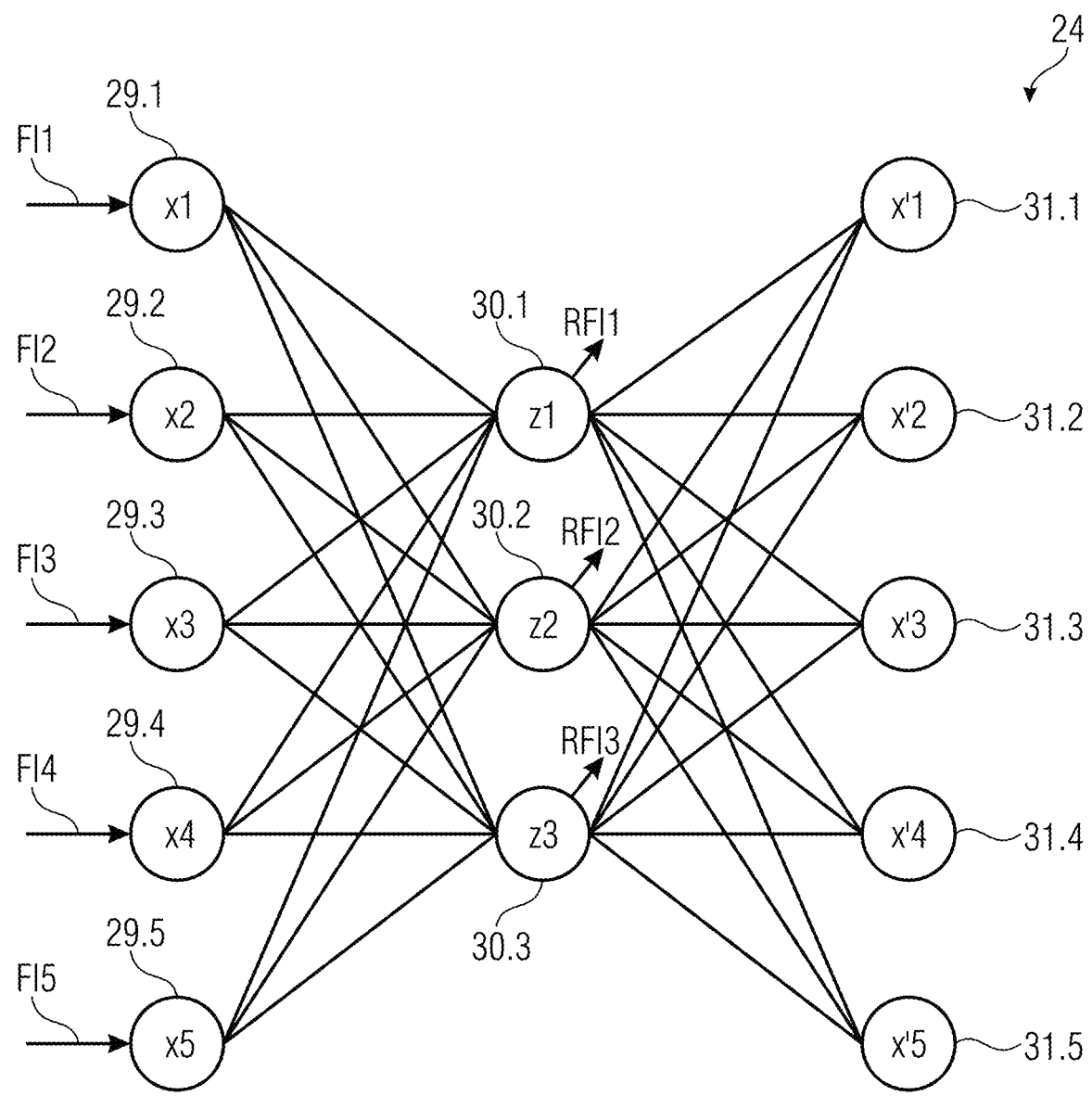
FIG. 9 illustrates an exemplary dimensionality reduction stage.

FIG. 9 illustrates an exemplary dimensionality reduction stage 24. In FIG. 9 the dimensionality reduction stage 24 is an auto-encoder 24. Five features FI1 to FI5 are fed to input nodes 29.1 to 29.5 of the auto-encoder 24. Three reduced features RFI1 to RFI3 are calculated and output at hidden nodes 30.1 to 30.3 of the auto encoder 24 so that the dimensionality is reduced from five to two. The output nodes 31.1 to 31.5 are of the same number as the input nodes 29.1 to 29.5 in order to allow unsupervised learning by trying to reproduce the input at input nodes 29.1 to 29.5 as the output at the output nodes 31.1 to 31.5 by minimizing the reconstruction error.

Figure 10:
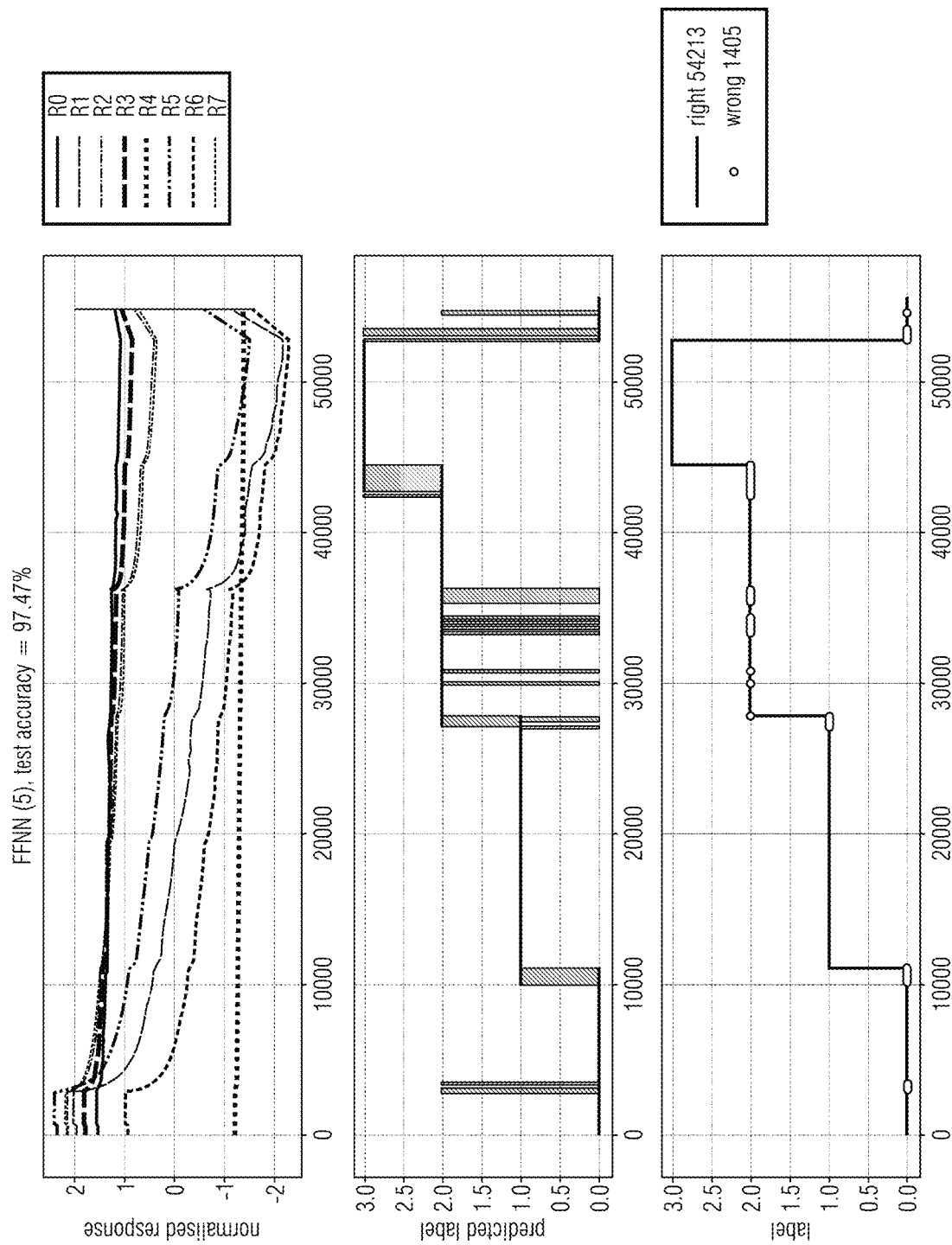
FIG. 10 illustrates an exemplary test accuracy achieved with a feed forward neural network.

FIG. 10 illustrates an exemplary test accuracy achieved with a feed forward neural network 11. Here, results corresponding to the processing blocks described above are provided. In most statistical models test accuracy increases as more features are added to the trained models TM and the feed forward neural network 11 outperformed other supervised methods. The low pass filter 25 always improved test accuracy by at least 0.25% and maximum test accuracy of 97.74% is reached after low pass filtering the feed forward neural network model using five neurons in the hidden layer and with filtered signal samples FSS, derivatives from the derivative calculation stage 20, phase space integral from the phase space integral calculation stage 21, time/space correlations from the correlation calculation stage 23 and dynamic moment from the dynamic moment calculation stage 22 as features FI. In this case, the time/space correlations and dynamic moments are reduced to two dimensions using principal component and a time delay of 30 samples and a moving window of 10 samples are used.

FIG. 10 shows the best test accuracy results for NO2 classification before applying a median filter as a low pass filter 25. Top graph shows the normalized sensor responses of the test set. Middle graph shows the predicted label by the classifier. The vertical axes represents the air quality index table with 0, 1, 2, and 3 indicate good, moderate, very poor and unhealthy concentration ranges respectively. The bottom graph shows the true label and the dots correspond to misclassified samples. Classification errors primarily occur at the air quality index concentration boundaries, the region were the classifiers struggle the most to distinguish new samples based on the trained ones.

Figure 11:
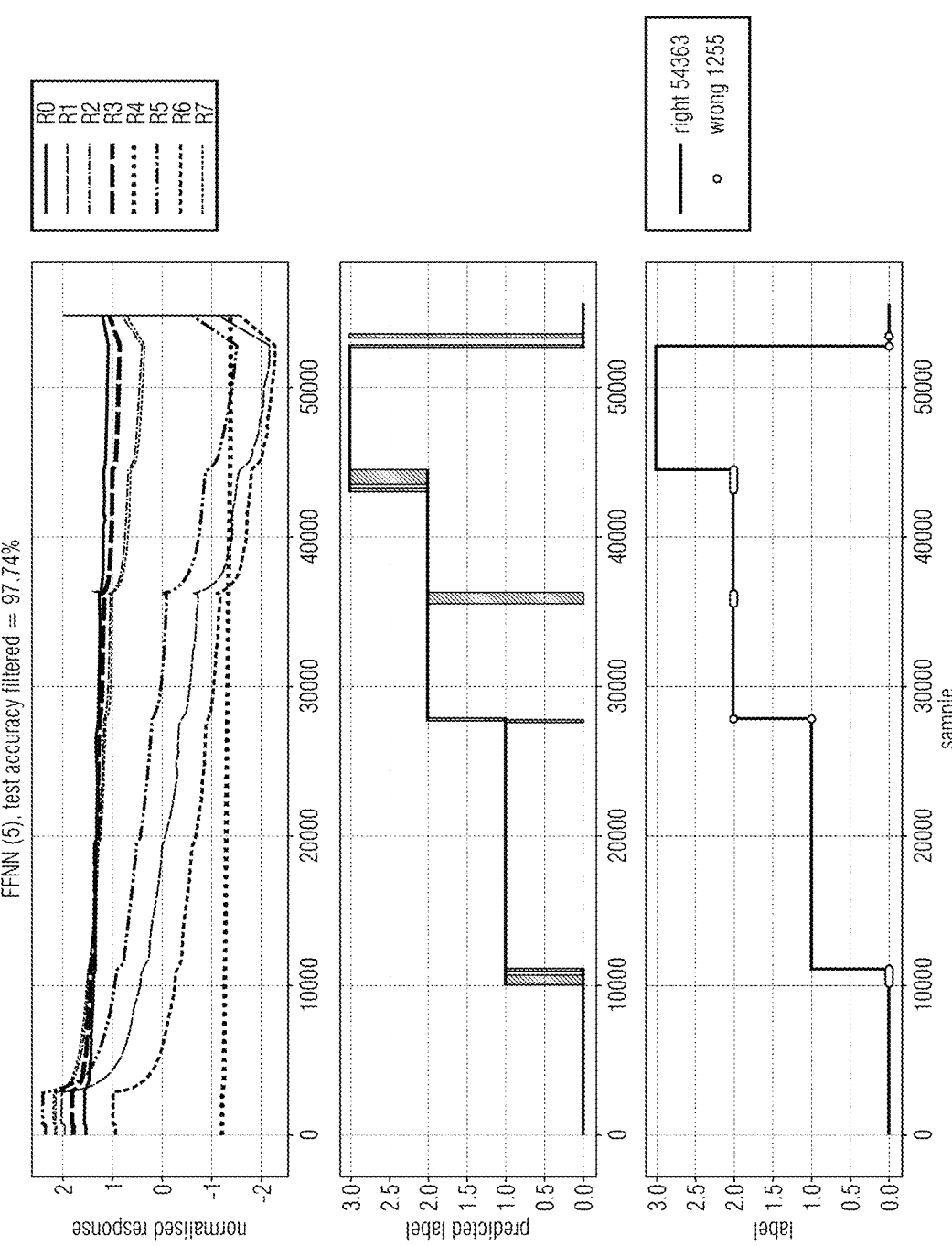
FIG. 11 illustrates a further exemplary test accuracy achieved with a feed forward neural network, wherein a median filter is used.

FIG. 11 illustrates a further exemplary test accuracy achieved with a feed forward neural network 11, wherein a median filter is used as a low pass filter 25. Figure ii shows how classification error decreases by 11% once the median filter is applied. The filter removes the most dispersed errors but can't remove the more clustered error particularly in the regions of air quality index boundaries. Interestingly, when the dynamic moments are reduced to 3 dimensions, a test accuracy of 93.87% is reached using a feed forward neural network 11 with only two neurons in the hidden layer. This is an indicator that increasing feature complexity, and therefore information available to the classifier, can help reduce model complexity.

Figure 12:
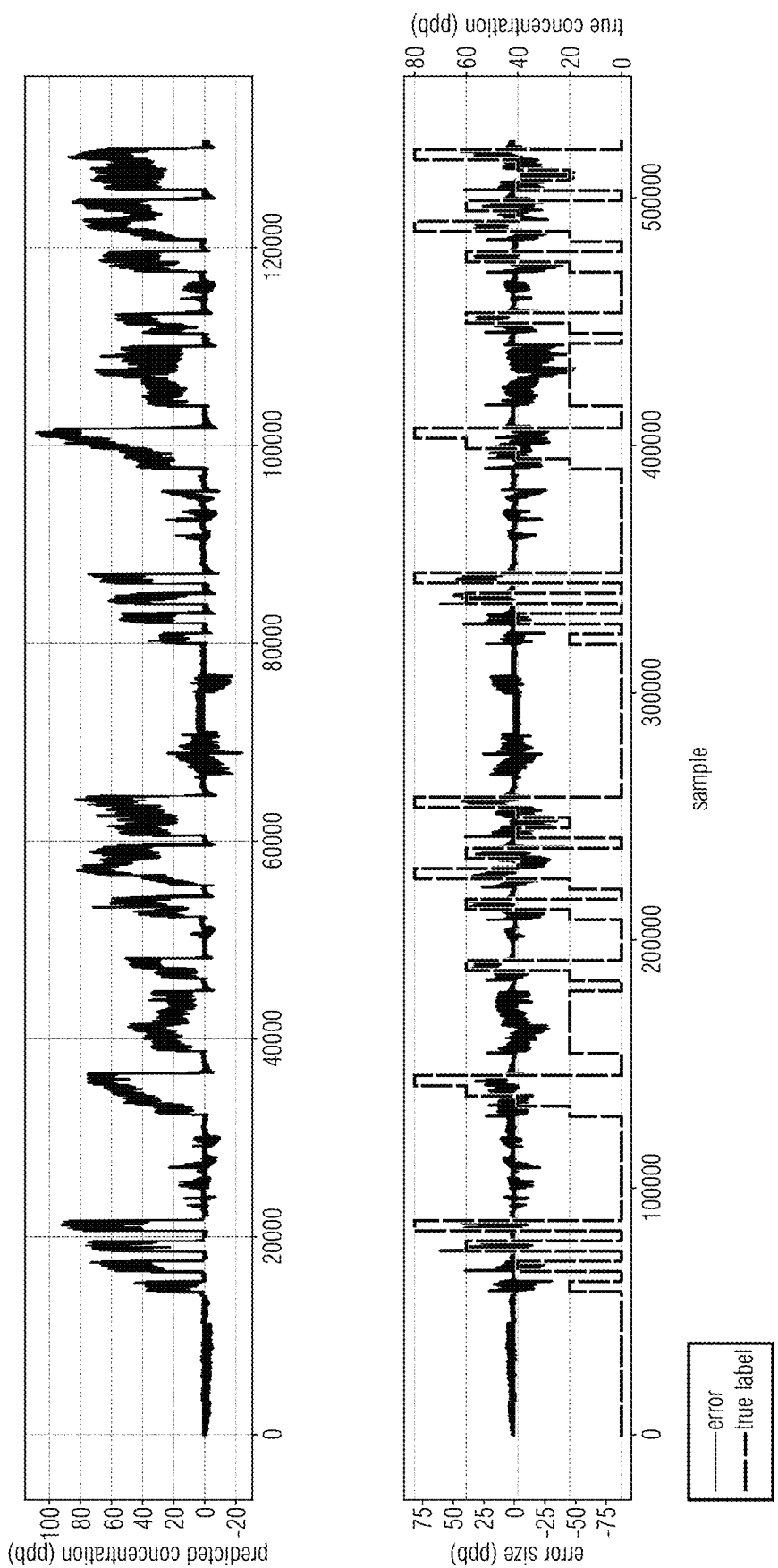
FIG. 12 illustrates regression results, wherein a multilayer perceptron regression is used.

FIG. 12 illustrates regression results, wherein a multilayer perceptron regression is used. Regression results for NO2 are shown in FIG. 12 for a multilayer perceptron regression applied to a gas mixture of NO2, O3 and CO. Some cross sensitivities are observed but the concentration trends are reproduced quite nicely by described algorithms.

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A gas sensing device for sensing one or more gases in a mixture of gases, the gas sensing device comprising:
   one or more chemo-resistive gas sensors, wherein each of the gas sensors is configured for generating signal samples corresponding to a concentration of one of the one or more gases in the mixture of gases, wherein the one or more gas sensors are alternately operated in recovery phases and in sense phases, wherein the signal samples of each of the gas sensors are generated during the sense phases;
   one or more heating elements for heating each of the gas sensors, wherein the one or more heating elements are brought to a first temperature during the recovery phases and to a second temperature during the sense phases, wherein the first temperature is higher than the second temperature;
   a preprocessing block configured for receiving the signal samples from each of the gas sensors and for filtering the received signal samples in order to generate filtered signal samples for each of the gas sensors;
   an information extraction block configured for receiving the filtered signal samples and for generating representations for the received filtered signal samples for each of the gas sensors based on dynamic characteristics of the received filtered signal samples of the respective gas sensor; and
   a decision making block configured for receiving the representations, wherein the decision making block comprises a trained model based algorithm stage having an input layer and an output layer, wherein the decision making block comprises one or more trained models for the algorithm stage, wherein the representations for each of the gas sensors are input to the input layer of the algorithm stage, wherein the decision making block creates for each of the gas sensors sensing results based on output values of the output layer of the algorithm stage, wherein the output values for each of the gas sensors are created by using at least one of the one or more trained models at the algorithm stage so that the output values for each of the gas sensors depend on the representations of each of the gas sensors.

2. A gas sensing device according to claim 1, wherein the gas sensing device comprises one or more auxiliary sensors, wherein each of the auxiliary sensors is configured for generating auxiliary signal samples corresponding to a physical quantity of operating conditions of the gas sensing device, and
   wherein the one or more auxiliary sensors comprise
   a first temperature sensor for generating first auxiliary signal samples of the auxiliary signal samples, which correspond to a temperature of the one or more heating elements, and/or a second temperature sensor for generating second auxiliary signal samples of the auxiliary signal samples, which correspond to an ambient temperature of the gas sensing device, and/or
   a humidity sensor for generating third auxiliary signal samples of the auxiliary signal samples, which correspond to an ambient humidity of the gas sensing device.

3. A gas sensing device according to claim 2, wherein the decision making block is configured for selecting one or more selected trained models from the one or more trained models based on the auxiliary signal samples of the one or more auxiliary sensors, wherein the output values for the one or more gas sensors are created by using the one or more selected trained models.

4. A gas sensing device according to claim 2, wherein the preprocessing block is configured for receiving the auxiliary signal samples from each of the auxiliary sensors and for filtering the received auxiliary signal samples in order to generate filtered auxiliary signal samples for each of the auxiliary sensors,
   wherein the information extraction block is configured for receiving the filtered auxiliary signal samples and for generating auxiliary representations for the received filtered auxiliary signal samples for each of the auxiliary sensors based on dynamic characteristics of the received filtered auxiliary signal samples of the respective auxiliary sensor, and
   wherein the decision making block is configured for inputting the auxiliary representations for each of the auxiliary sensors to the input layer of the algorithm stage so that the output values for the one or more gas sensors depend on the auxiliary representations of each of the auxiliary sensors.

5. A gas sensing device according to claim 2, wherein the pre-processing block comprises a defect detection stage configured for a detection of defects of the gas sensing device, wherein the detection is based on the auxiliary signal samples of one or of the more auxiliary sensors.

6. A gas sensing device according to claim 1, wherein the algorithm stage comprises a neural network using the one or more trained models and/or a random decision forest using the one or more trained models.

7. A gas sensing device according to claim 1, wherein the one or more trained models comprise one or more trained multiple-output models having a plurality of outputs, wherein for all of the gas sensors the output values for the respective gas sensor are created by using one of the trained multiple-output models at the algorithm stage, wherein each of the output values is created at a different output of the plurality of outputs.

8. A gas sensing device according to claim 1, wherein for each of the gas sensors the one or more trained models comprise one or more trained single-output models having a single output, wherein the output values for different gas sensors of the gas sensors are created by using different single-output models of the trained single-output models at the algorithm stage.

9. A gas sensing device according to claim 1, wherein the preprocessing block comprises a baseline manipulation stage configured for transforming the signal samples of each of the gas sensors into a relative resistance change according to a baseline of the signal samples of the respective gas sensor.

10. A gas sensing device according to claim 1, wherein the preprocessing block comprises an artefact detection stage configured for a detection artefacts in the signal samples of each of the gas sensors, wherein the detection for each of the gas sensors is based on comparing of sequential signal samples of the respective gas sensor.

11. A gas sensing device according to claim 1, wherein the preprocessing block comprises a moving mean filter stage configured for reducing noise in the filtered signal samples for each of the gas sensors.

12. A gas sensing device according to claim 1, wherein the information extraction block comprises one or more feature extraction stages, wherein each of the feature extraction stages is configured for calculating a feature of one of the filtered signal samples for each of the gas sensors, wherein each of the features refers to the dynamic characteristics of the received filtered signal samples of the respective gas sensor.

13. A gas sensing device according to claim 12, wherein the feature extraction stages comprise a derivative calculation stage configured for calculating a derivative of the one of the filtered signal samples for each of the gas sensors, wherein the derivative is one of the features of the one of the filtered signal samples.

14. A gas sensing device according to claim 12, wherein the feature extraction stages comprise a phase space integral calculation stage configured for calculating a phase space integral of the one of the filtered signal samples for each of the gas sensors, wherein the phase space integral is one of the features of the one of the filtered signal samples.

15. A gas sensing device according to claim 12, wherein the feature extraction stages comprise a correlation calculation stage configured for calculating of
a time correlation for each of the gas sensors between the one of the filtered signal samples and a previous filtered signal sample of the signal samples of the respective gas sensor, wherein the time correlation is one of the features of the one of the filtered signal samples, and/or
a spatial correlation between the one of the filtered signal samples and one of the filtered signal samples of another of the gas sensors, wherein the spatial correlation is one of the features of the one of the filtered signal samples.

16. A gas sensing device according to claim 12, wherein the feature extraction stages comprise a dynamic moment calculation stage configured for calculating of a dynamic moment of the one of the filtered signal samples for each of the gas sensors, wherein the dynamic moment is one of the features of the one of the filtered signal samples.

17. A gas sensing device according to claim 12, wherein the information extraction block is configured in such way that one of the representations comprises all of the features of the one of the filtered signal samples.

18. A gas sensing device according to claim 12, wherein the information extraction block comprises a dimensionality reduction stage, wherein each of a plurality of the features of the one of the filtered signal samples is fed to dimensionality reduction stage, wherein the dimensionality reduction stage is configured to output one or more reduced features based on the plurality of the features fed to the dimensionality reduction stage, wherein a number of the reduced features is smaller than a number of the features fed to the dimensionality reduction stage, wherein a redundancy of the reduced features is lower than a redundancy of the features fed to the dimensionality reduction stage, wherein the information extraction block is configured in such way that one of the representations comprises all of the reduced features of the one of the filtered signal samples.

19. A gas sensing device according to claim 1, wherein the decision making block comprises a low pass filter for filtering the output values of the output layer of the algorithm stage for each of the gas sensors, wherein the sensing results are output values of the low pass filter.

20. A method for operating a gas sensing device for sensing one or more gases in a mixture of gases, the gas sensing device comprising one or more chemo-resistive gas sensors, wherein the method comprises:
using each of the gas sensors for generating signal samples corresponding to a concentration of one of the one or more gases in the mixture of gases, wherein the one or more gas sensors are alternately operated in recovery phases and in sense phases, wherein the signal samples of each of the sensors are generated during the sense phases;
heating each of the gas sensors by using one or more heating elements, wherein the one or more heating elements are brought to a first temperature during the recovery phases and to a second temperature during the sense phases, wherein the first temperature is higher than the second temperature;
using a preprocessing block for receiving the signal samples from each of the gas sensors and for filtering the received signal samples in order to generate filtered signal samples for each of the gas sensors;
using an information extraction block for receiving the filtered signal samples and for generating representations for the received filtered signal samples for each of the gas sensors based on dynamic characteristics of the received filtered signal samples of the respective gas sensor; and
using a decision making block, which comprises a trained model based algorithm stage and one or more trained models for the algorithm stage, wherein the algorithm stage has an input layer and an output layer,
for receiving the representations, wherein the representations for each of the gas sensors are input to the input layer of the algorithm stage,
for creating for each of the gas sensors sensing results based on output values of the output layer of the algorithm stage, and wherein the output values for the one or more gas sensors are created by using at least one of the one or more trained models at the algorithm stage so that the output values for each gas sensor of the one or more gas sensors depend on the representations of each of the gas sensors.

\* \* \* \* \*